(12) United States Patent
Sobotka et al.

(10) Patent No.: US 11,673,006 B2
(45) Date of Patent: Jun. 13, 2023

(54) CATHETER-BASED DEVICES AND ASSOCIATED METHODS FOR IMMUNE SYSTEM NEUROMODULATION

(71) Applicant: MEDTRONIC IRELAND MANUFACTURING UNLIMITED COMPANY, Dublin (IE)

(72) Inventors: Paul Sobotka, West St. Paul, MN (US); Neil Barman, Mountain View, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 234 days.

(21) Appl. No.: 17/018,625

(22) Filed: Sep. 11, 2020

(65) Prior Publication Data

US 2021/0001155 A1   Jan. 7, 2021

Related U.S. Application Data

(63) Continuation of application No. 15/788,161, filed on Oct. 19, 2017, now abandoned, which is a
(Continued)

(51) Int. Cl.
*A61N 7/00* (2006.01)
*A61B 18/14* (2006.01)
(Continued)

(52) U.S. Cl.
CPC ........ *A61N 7/00* (2013.01); *A61B 17/320068* (2013.01); *A61B 18/02* (2013.01);
(Continued)

(58) Field of Classification Search
CPC .......... A61N 7/00; A61N 1/0551; A61N 1/40; A61N 5/045; A61N 5/0601; A61N 5/0622;
(Continued)

(56) References Cited

U.S. PATENT DOCUMENTS

| | | | |
|---|---|---|---|
| 2005/0021092 A1* | 1/2005 | Yun | A61N 1/326 607/3 |
| 2005/0075702 A1* | 4/2005 | Shafer | A61N 1/36071 607/72 |

(Continued)

*Primary Examiner* — Amanda K Hulbert
*Assistant Examiner* — Natasha Patel
(74) *Attorney, Agent, or Firm* — Shumaker & Sieffert, P.A.

(57) ABSTRACT

Catheter-based devices and associated methods for immune system neuromodulation of human patients are disclosed herein. One aspect of the present technology is directed to methods of treating a human patient diagnosed with an immune system condition. The methods can include intravascularly positioning a neuromodulation catheter within a blood vessel proximate to neural fibers innervating an immune system organ of the patient. The method also includes reducing sympathetic neural activity in the patient by delivering energy to the neural fibers innervating the immune system organ via the neuromodulation catheter. Reducing sympathetic neural activity improves a measurable physiological parameter corresponding to the immune system condition of the patient.

20 Claims, 4 Drawing Sheets

Related U.S. Application Data continuation of application No. 15/372,305, filed on Dec. 7, 2016, now abandoned, which is a continuation of application No. 14/379,886, filed as application No. PCT/US2013/029685 on Mar. 7, 2013, now abandoned.

(60) Provisional application No. 61/608,422, filed on Mar. 8, 2012.

(51) Int. Cl.
| | | |
|---|---|---|
| *A61N 7/02* | (2006.01) | |
| *A61B 18/02* | (2006.01) | |
| *A61B 18/18* | (2006.01) | |
| *A61B 18/20* | (2006.01) | |
| *A61B 17/32* | (2006.01) | |
| *A61N 1/05* | (2006.01) | |
| *A61N 1/40* | (2006.01) | |
| *A61N 5/04* | (2006.01) | |
| *A61N 5/06* | (2006.01) | |
| *A61B 18/00* | (2006.01) | |
| *A61N 1/20* | (2006.01) | |
| *A61N 1/36* | (2006.01) | |

(52) U.S. Cl.
CPC .......... *A61B 18/14* (2013.01); *A61B 18/1492* (2013.01); *A61B 18/1815* (2013.01); *A61B 18/20* (2013.01); *A61N 1/0551* (2013.01); *A61N 1/40* (2013.01); *A61N 5/045* (2013.01); *A61N 5/0601* (2013.01); *A61N 5/0622* (2013.01); *A61N 7/02* (2013.01); *A61B 2018/0016* (2013.01); *A61B 2018/00214* (2013.01); *A61B 2018/00404* (2013.01); *A61B 2018/00434* (2013.01); *A61B 2018/00577* (2013.01); *A61B 2018/00642* (2013.01); *A61B 2018/0212* (2013.01); *A61B 2018/1861* (2013.01); *A61N 1/205* (2013.01); *A61N 1/36017* (2013.01); *A61N 2005/0612* (2013.01); *A61N 2007/003* (2013.01); *A61N 2007/0017* (2013.01); *A61N 2007/0021* (2013.01); *A61N 2007/0043* (2013.01)

(58) Field of Classification Search
CPC ...... A61N 7/02; A61N 1/205; A61N 1/36017; A61N 2005/0612; A61N 2007/0017; A61N 2007/0021; A61N 2007/003; A61N 2007/0043; A61B 17/320068; A61B 18/02; A61B 18/14; A61B 18/1492; A61B 18/1815; A61B 18/20; A61B 2018/0016; A61B 2018/00214; A61B 2018/00404; A61B 2018/00434; A61B 2018/00577; A61B 2018/00642; A61B 2018/0212; A61B 2018/1861
See application file for complete search history.

(56) References Cited

U.S. PATENT DOCUMENTS

| | | | |
|---|---|---|---|
| 2009/0192570 A1* | 7/2009 | Jaax | A61N 1/05 607/46 |
| 2010/0168731 A1* | 7/2010 | Wu | A61B 18/1206 606/33 |

* cited by examiner

CATHETER-BASED DEVICES AND ASSOCIATED METHODS FOR IMMUNE SYSTEM NEUROMODULATION

CROSS-REFERENCE TO RELATED APPLICATIONS

This application is a continuation of U.S. patent application Ser. No. 15/788,161, titled "CATHETER-BASED DEVICES AND ASSOCIATED METHODS FOR IMMUNE SYSTEM NEUROMODULATION", filed on Oct. 19, 2017, which is a continuation of U.S. patent application Ser. No. 15/372,305, titled "CATHETER-BASED DEVICES AND ASSOCIATED METHODS FOR IMMUNE SYSTEM NEUROMODULATION", filed on Dec. 7, 2016, which is a continuation of U.S. patent application Ser. No. 14/379,886, titled "IMMUNE SYSTEM NEUROMODULATION AND ASSOCIATED SYSTEMS AND METHODS", filed on Aug. 20, 2014, which is a 371 National Stage of International Application No. PCT/US2013/029685, titled "IMMUNE SYSTEM NEUROMODULATION AND ASSOCIATED SYSTEMS AND METHODS", filed on Mar. 7, 2013, which claims priority to and the benefit of U.S. Provisional Patent Application No. 61/608,422, titled "IMMUNE SYSTEM NEUROMODULATION AND ASSOCIATED SYSTEMS AND METHODS", filed on Mar. 8, 2012, the disclosures of which are all incorporated by reference herein in their entireties.

TECHNICAL FIELD

The present technology relates generally to modulation of nerves of immune system organs and associated systems and methods.

BACKGROUND

The sympathetic nervous system (SNS) is a primarily involuntary bodily control system typically associated with stress responses. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. Signals sent via these and other fibers can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology is generally directed to modulation of nerves of one or more immune system organs to treat immune system conditions, conditions associated with sympathetic activity (e.g., overactivity or hyperactivity) in immune system organs, and/or conditions associated with central sympathetic activity (e.g., overactivity or hyperactivity). For example, several embodiments are directed to modulation of nerves of one or more immune system organs to treat autoimmune conditions and related conditions. As discussed in greater detail below, immune system neuromodulation can include rendering neural fibers inert, inactive, or otherwise completely or partially reduced in function. This result can be electrically-induced, thermally-induced, chemically-induced, or induced by another mechanism during an immune system neuromodulation procedure, e.g., a procedure including percutaneous transluminal intravascular access.

Specific details of several embodiments of the present technology are described herein with reference to FIGS. 1A-3. The embodiments can include, for example, modulating nerves proximate (e.g., at or near) the splenic artery, the splenic veins, the thymic artery, the thymic veins, another portion of a vessel or duct of an immune system organ, and/or other suitable structures. Although many of the embodiments are described herein with respect to thermally-induced, electrically-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1A-3.

As used herein, the terms "distal" and "proximal" define a position or direction with respect to the treating clinician or clinician's control device. "Proximal" and "proximally" can refer to a position near or in a direction toward the clinician or clinician's control device. "Distal" or "distally" can refer to a position distant from or in a direction away from the clinician or clinician's control device.

I. Immune System

The human immune system has two categories of defenses: innate and adaptive. The innate immune system response is non-specific, meaning it responds to pathogens in a generic way and does not confer long-lasting immunity against a pathogen. The innate system includes both humoral and chemical barriers and cellular barriers that utilize phagocytes (macrophages, neutrophils, and dendritic cells), mast cells, eosinophils, basophils, and natural killer cells. The adaptive immune system allows for stronger immune responses and immunological memory, meaning that a particular pathogen is remembered based on specific antigens. The adaptive immune system requires recognition of non-self-antigens during a process called antigen recognition. The primary cells of the adaptive immune system are lymphocytes, of which B cells and T cells are the most common.

Organs involved in the immune system response include the spleen, thymus, lymph nodes, and bone marrow. The spleen is located in the left upper quadrant of the abdomen, the thymus is located atop the pericardium within the chest cavity, and the lymph nodes and bone marrow are distributed throughout the body. The sympathetic nervous system appears to provide most of the efferent autonomic control over the immune system organs, while most direct afferent input from the immune system appears to come from the bone marrow and lymph nodes.

II. Autoimmune Conditions

Autoimmune conditions are the result of an inappropriate immune response against substances and tissues normally present in the body. Specialized cells located in the thymus and bone marrow normally present immature lymphocytes with self-antigens and eliminate those that recognize self-antigens. In subjects with autoimmune conditions, however, the immune system is unable to tell the difference between healthy body tissue and foreign antigens and, therefore, attacks the healthy body tissue. This can result in a hypersensitivity reaction similar to the response in allergic conditions.

Autoimmune condition flares are often linked to psychological stressors, and the reaction to such stressors appears to have a neural component. For example, adaptational stress responses involve activation of both the hypothalamus-pituitary-adrenal (HPA) axis and the autonomic nervous system (ANS), and both of these axes are thought to communicate bidirectionally with the immune system. Activation of the HPA axis and ANS in response to an external stressor results in the release of cortisol and catecholamines. These stress hormones generally downregulate immune and inflammatory responses, but also influence the central nervous system.

The central sympathetic system regulates some aspects of the immune system, e.g., T-cell differentiation. Activation of the sympathetic nervous system primarily inhibits the activity of cells associated with the innate immune system while either enhancing or inhibiting the activity of cells associated with the acquired/adaptive immune system. The specific role of the sympathetic nerves depends on a variety of factors. For example, in a mouse model of systemic lupus erythematosus (SLE), alterations in sympathetic innervation have been linked to disease pathogenesis, which strongly supports the hypothesis that the sympathetic nervous system can modulate expression of autoimmune lymphoproliferative disease.

Current therapies for autoimmune conditions include anti-inflammatory drugs such as steroids and immunosuppressive agents that locally or systemically modify the immune system (e.g., TNFa antagonists and B cell depleting agents). However, these therapies generally require life-long adherence, and many patients still experience acute disease flares.

III. Immune System Neuromodulation

Immune system neuromodulation is the partial or complete incapacitation or other effective disruption or regulation of immune system nerves, e.g., nerves terminating in or originating from one or more immune system organs (including, but not limited to, the spleen, lymph nodes, bone marrow, thymus, and other suitable organs) or in structures closely associated with the immune system organs. In particular, immune system neuromodulation comprises inhibiting, reducing, blocking, pacing, upregulating, and/or downregulating neural communication along neural fibers (e.g., efferent and/or afferent neural fibers) innervating one or more immune system organs. Such incapacitation, disruption, and/or regulation can be long-term (e.g., permanent or for periods of months, years, or decades) or short-term (e.g., for periods of minutes, hours, days, or weeks). While long-term disruption of the immune system nerves can be desirable for alleviating symptoms and other sequelae associated with autoimmune conditions and other immune system conditions over longer periods of time, short-term modulation of the immune system nerves may also be desirable, for example, to generate a temporary reduction in symptoms or to address other issues.

As noted previously, there is significant sympathetic input to all components of the immune system, and immune system autonomic neural activity (increased sympathetic drive or decreased parasympathetic drive, or a change in the ratio thereof) can cause or exacerbate various immune system conditions, including for example autoimmune conditions such as multiple sclerosis, lupus, psoriasis, and other immune system conditions. Immune system neuromodulation is expected to be useful in treating these conditions, for example by reducing mechanisms of inflammation and modulating the immune response. For example, the disclosed methods and systems for immune system neuromodulation are expected to cause an improvement (e.g., a reduction) in one or more markers of inflammation, (e.g., interleukins, high-sensitivity C-reactive proteins, erythrocyte sedimentation rate (ESR), heat shock proteins, and/or other suitable markers) in patients diagnosed with autoimmune conditions and/or other patients. Similarly, the disclosed methods and systems for immune system neuromodulation are expected to reduce the need for steroid or immune modulating agents (e.g., tumor necrosis factor inhibitors) in patients diagnosed with autoimmune diseases and/or other patients.

Furthermore, afferent sympathetic activity from immune system organs can contribute to central sympathetic tone or drive. Accordingly, immune system neuromodulation is expected to be useful in treating clinical conditions associated with central sympathetic activity (e.g., overactivity or hyperactivity), particularly conditions associated with central sympathetic overstimulation. Conditions associated with central sympathetic activity (e.g., overactivity or hyperactivity) include, for example, hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

In certain patients, reducing sympathetic drive in one or more immune system organs, reducing central sympathetic drive, and/or other benefits from immune system neuromodulation are expected to outweigh the complete or partial loss of sympathetic-nerve functionality in treated immune system organs.

Several properties of the immune system organ vasculature may inform the design of treatment devices and associated methods for achieving immune system neuromodulation (e.g., via intravascular access), and impose specific design requirements for such devices. Specific design requirements may include accessing the immune system organ blood vessels (e.g., splenic artery, splenic vein, thymic artery, thymic vein), facilitating stable contact between the energy delivery elements of such devices and a luminal surface or wall of the immune system organ blood vessel, and/or effectively modulating the immune system nerves with the neuromodulatory apparatus.

Potential targets for immune system neuromodulation include nerves innervating immune system organs such as the spleen, thymus, and lymph nodes. Among the immune system organs, the spleen can be a particularly well-suited target for neuromodulation. In addition to acting as a blood filter and blood reserve, the spleen plays an important role in the immune system by synthesizing antibodies in its white pulp and removing antibody-coated bacteria and blood cells by way of blood and lymph node circulation. Further, the spleen contains in its blood reserves half of the body's monocytes, which turn into dendritic cells upon migrating to injured tissue.

Splenic nerve activity can have a variety of effects on other organs and on the central sympathetic system. For example, the splenorenal reflex can include increased sympathetic efferent communication to renal nerves in response to increased afferent communication from splenic nerves. The increased efferent communication to renal nerves can decrease renal blood flow and trigger the renin-angiotensin-aldosterone system, ultimately causing an increase in blood pressure. Splenic afferent activity also can affect cardiopulmonary sympathetic nerve activity. The mechanism of the sympathetic responses to splenic nerve activity can originate, for example, in the spine or the brain. Increases in splenic afferent activity can occur, for example, when mechanoreceptors of the spleen sense increases in postcapillary venous pressure. Splenic efferent activity also can have systemic significance. For example, the spleen can regulate blood volume, e.g., by releasing blood to counteract hypovolemia and/or causing fluid to move from blood into lymph to counteract hypervolemia. In addition to its role in treating autoimmune conditions and other immune system conditions, splenic neuromodulation may have anticoagulant effects. Therefore, splenic neuromodulation may also be used in situations where anticoagulant or antiplatelet effects are desired.

A Selected Examples of Neuromodulation Modalities

Various techniques can be used to partially or completely incapacitate neural pathways, such as those innervating the immune system organs. Immune system neuromodulation in accordance with embodiments of the present technology, for example, can be electrically-induced, thermally-induced, chemically-induced, or induced in another suitable manner or combination of manners at one or more suitable treatment locations during a treatment procedure. For example, the purposeful application of radio frequency (RF) energy (monopolar and/or bipolar), pulsed RF energy, microwave energy, optical energy, ultrasound energy (e.g., intravascularly delivered ultrasound, extracorporeal ultrasound, high-intensity focused ultrasound (HIFU)), magnetic energy, direct heat, cryotherapeutic energy, chemicals (e.g., drugs or other agents), or combinations thereof to tissue at a treatment location can induce one or more desired effects at the treatment location, e.g., broadly across the treatment location or at localized regions of the treatment location.

Figure 1A:
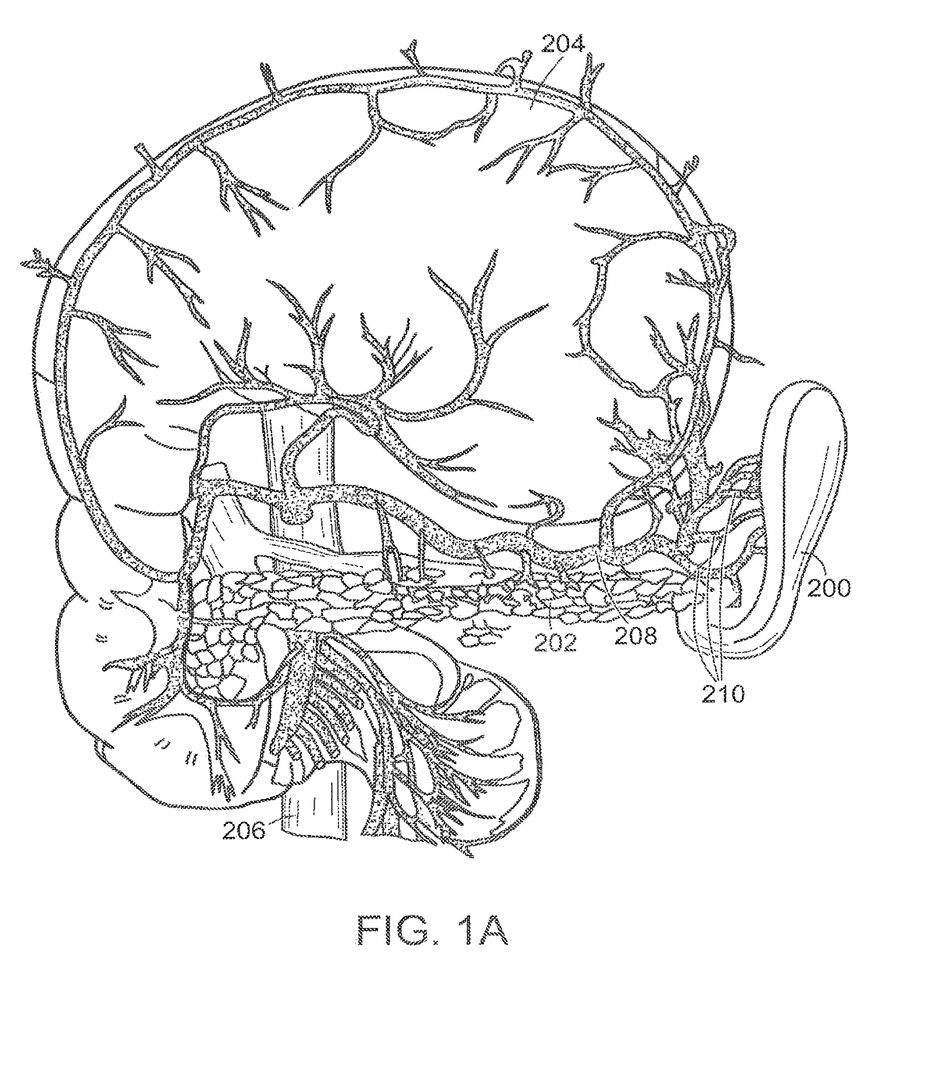
FIG. 1A is an anatomical view illustrating abdominal organs of a human patient, including a spleen, a splenic artery, and nearby organs and vessels.

FIG. 1A is an anatomical view illustrating the abdominal organs, including the spleen 20, splenic artery 28, and splenic branch arteries 21. Referring to FIG. 1A, treatment procedures in accordance with embodiments of the present technology can include applying a treatment modality at one or more treatment locations proximate a structure having a relatively high concentration of immune system nerves. In some embodiments, for example, the treatment locations can be proximate portions of the splenic artery 28, an ostium of the splenic artery 28, a splenic branch artery 21, an ostium of a splenic branch artery 21, the splenic vein, an ostium of the splenic vein, or a branch of the splenic vein, another portion of a vessel or duct of an immune system organ, and/or another suitable structure.

Figure 1B:
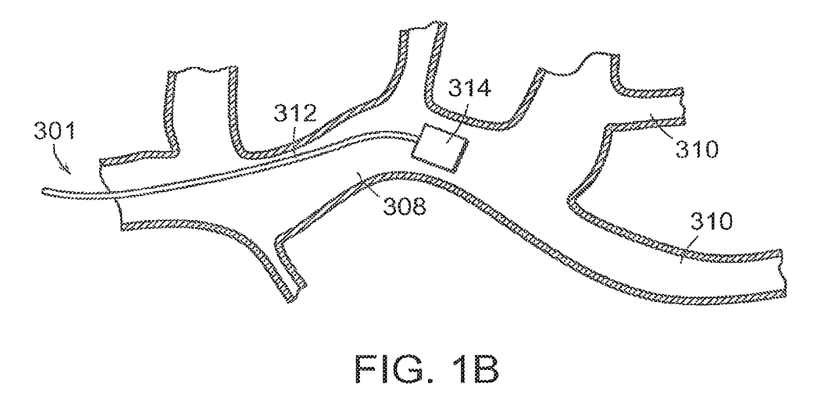
FIG. 1B is a partially cross-sectional view illustrating neuromodulation at a treatment location within a splenic artery in accordance with an embodiment of the present technology.
Figure 1C:
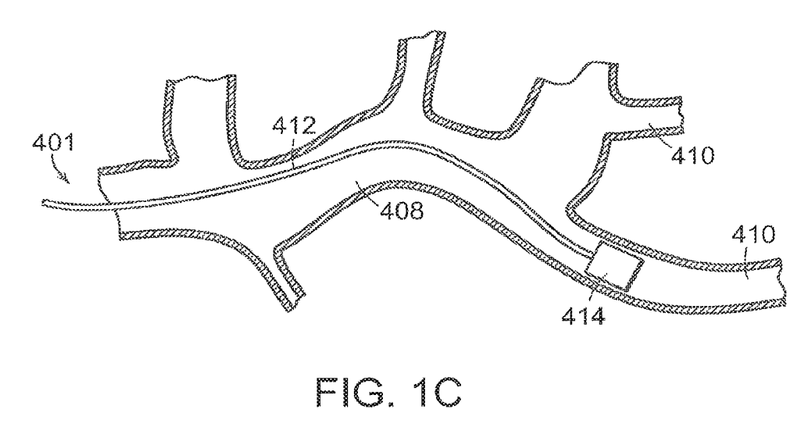
FIG. 1C is a partially cross-sectional view illustrating neuromodulation at a treatment location within a splenic branch artery in accordance with an embodiment of the present technology.

FIGS. 1B and 1C, for example, are cross-sectional views illustrating, respectively, neuromodulation at treatment locations within the splenic artery and a splenic branch artery. As shown in FIG. 1B, a treatment device 31 including a shaft 32 and a therapeutic element 34 can be extended toward the splenic artery 38 to locate the therapeutic element 34 at a treatment location within the splenic artery 38. Similarly, as shown in FIG. 1C, a treatment device 41 can be extended toward a splenic branch artery 40 to locate the therapeutic element 44 at a treatment location within the splenic branch artery 40. The therapeutic element 34 or 44 can be configured for neuromodulation at the treatment locations via a suitable treatment modality, e.g., cryotherapeutic, direct heat, electrode-based, transducer-based, chemical-based, or another suitable treatment modality.

The treatment location can be proximate (e.g., at or near) a vessel or duct wall (e.g., a wall of the splenic artery, the splenic vein, a splenic branch artery, another portion of a vessel or duct of an immune system organ, and/or another suitable structure), and the treated tissue can include tissue proximate the treatment location. For example, with regard to the splenic artery 38, a treatment procedure can include modulating nerves in the splenic plexus, which lay at least partially within or adjacent to the adventitia of the splenic artery. In some embodiments it may be desirable to modulate immune system nerves from a treatment location within a vessel and in close proximity to an immune system organ, e.g., closer to the immune system organ than to a trunk of the vessel. This can increase the likelihood of modulating nerves specific to the immune system organ, while decreasing the likelihood of modulating nerves that extend to other organs. Vessels can decrease in diameter and become more tortuous as they extend toward an immune system organ. Accordingly, modulating immune system nerves from a treatment location in close proximity to an immune system organ can include using a device (e.g., a treatment device 31 or 41) having size, flexibility, torque-ability, kink resistance, and/or other characteristics suitable for accessing narrow and/or tortuous portions of vessels.

In some embodiments, the purposeful application of energy (e.g., electrical energy, thermal energy, etc.) to tissue can induce one or more desired thermal heating and/or cooling effects on localized regions of the splenic artery, for example, and adjacent regions along all or a portion of the splenic plexus, which lay at least partially within or adjacent to the adventitia of the splenic artery. Some embodiments of the present technology, for example, include cryotherapeutic immune system neuromodulation (alone or in combination with another treatment modality), which can include cooling tissue at a treatment location in a manner that modulates neural function. For example, sufficiently cooling at least a portion of a sympathetic nerve can slow or potentially block conduction of neural signals to produce a prolonged or permanent reduction in sympathetic activity. The mechanisms of cryotherapeutic tissue damage include, for example, direct cell injury (e.g., necrosis), vascular or luminal injury (e.g., starving the cells of nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a vessel or duct wall such that proximate (e.g., adjacent) tissue is effectively cooled to a depth where sympathetic nerves reside. For example, a cooling structure can be cooled to the extent that it causes therapeutically effective cryogenic neuromodulation. Sufficiently cooling at least a portion of a sympathetic immune system nerve may slow or potentially block conduction of neural signals to produce a prolonged or permanent reduction in immune system sympathetic activity. In some embodiments, a cryotherapeutic treatment modality can include cooling that is not configured to cause neuromodulation. For example, the cooling can be at or above cryogenic temperatures and can be used to control neuromodulation via another treatment modality, e.g., to reduce damage to non-targeted tissue when targeted tissue adjacent to the non-targeted tissue is heated.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel or duct stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause the spleen and other immune system organs to rise and fall and thereby move their associated vessels and ducts. In addition, blood flow is pulsatile and can cause structures to pulse. Cryogenic adhesion also can facilitate intravascular and intraluminal positioning, particularly in relatively small structures (e.g., relatively short arteries) in which stable positioning can be difficult to achieve.

As an alternative to or in conjunction with cryotherapeutic cooling, other suitable energy delivery techniques, such as electrode-based or transducer-based approaches, can be used for therapeutically-effective immune system neuromodulation. Electrode-based or transducer-based treatment, for example, can include delivering electrical energy and/or another form of energy to tissue and/or heating tissue at a treatment location in a manner that modulates neural function. For example, sufficiently stimulating and/or heating at least a portion of a sympathetic immune system nerve can slow or potentially block conduction of neural signals to produce a prolonged or permanent reduction in sympathetic activity. As noted previously, suitable energy modalities include, for example, RF energy (monopolar and/or bipolar), pulsed RF energy, microwave energy, ultrasound energy (e.g., intravascularly delivered ultrasound, extracorporeal ultrasound, HIFU), laser energy, optical energy, magnetic energy, direct heat, or other suitable energy modalities alone or in combination. Where a system uses a monopolar configuration, a return electrode or ground patch fixed externally on the subject can be used. Moreover, electrodes (or other energy delivery elements) can be used alone or with other electrodes in a multi-electrode array. Examples of suitable multi-electrode devices are described in U.S. patent application Ser. No. 14/281,360, filed Oct. 25, 2011, and incorporated herein by reference in its entirety. Other suitable devices and technologies, such as cryotherapeutic devices, are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties.

Thermal effects can include both thermal ablation and non-ablative thermal alteration or damage (e.g., via sustained heating and/or resistive heating) to partially or completely disrupt the ability of a nerve to transmit a signal. Desired thermal heating effects may include, for example, raising the temperature of target neural fibers to a target temperature to achieve non-ablative thermal alteration, or to or above a higher target temperature to achieve ablative thermal alteration. For example, a target temperature for non-ablative thermal alteration may be greater than body temperature (e.g., about 37° C.) but less than about 45° C., while a target temperature for ablative thermal alteration may be greater than about 45° C. Exposure to thermal energy between about body temperature and about 45° C. may induce non-ablative thermal alteration via moderate heating of target neural fibers or of vascular or luminal structures that perfuse the target neural fibers. In cases where vascular or luminal structures are affected, the target neural fibers may be denied perfusion, resulting in necrosis of the neural tissue. For example, this may induce non-ablative thermal alteration in the fibers or structures. Exposure to thermal energy greater than about 45° C. (e.g., greater than about 60° C.) may induce thermal ablation via substantial heating of target neural fibers or of vascular or luminal structures that perfuse the target fibers. In some patients, it may be desirable to achieve temperatures that thermally ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, immune system neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. For example, the chemical(s) can be guanethidine, ethanol, phenol, vincristine, a neurotoxin, or another suitable agent selected to alter, damage, or disrupt nerves. In some embodiments, energy (e.g., light, ultrasound, or another suitable type of energy) can be used to activate the chemical(s) and/or to cause the chemical(s) to become more bioavailable. A variety of suitable techniques can be used to deliver chemicals to tissue at a treatment location. For example, chemicals can be delivered via one or more devices, such as needles originating outside the body or within the vasculature or delivery pumps (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a vessel or duct wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

In some embodiments, a treatment procedure can include applying a suitable treatment modality at a treatment location in a testing step followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate to the treatment location are suitable for modulation. Performing a testing step can be particularly useful for treatment procedures in which targeted nerves are closely associated with nerves that could cause undesirable side effects if modulated during a subsequent treatment step.

IV. Methods for Treatment of Immune System Conditions

Sympathetic neural activity in immune system organs can cause or exacerbate immune system conditions, e.g., autoimmune conditions such as multiple sclerosis, lupus, psoriasis, and other immune system conditions. As noted previously, disclosed herein are several embodiments of methods directed to treatment of autoimmune conditions and other immune system conditions, as well as conditions associated with sympathetic activity (e.g., overactivity or hyperactivity) in the immune system organs and/or conditions associated with central sympathetic activity (e.g., overactivity or hyperactivity), using immune system neuromodulation. The methods disclosed herein may provide various advantages over a number of conventional approaches and techniques in that they allow for the potential targeting of elevated sympathetic drive, which may either be a cause of autoimmune conditions and other immune system conditions or a key mediator of the multiple manifestations of these conditions. Also, the disclosed methods provide for localized treatment and limited duration treatment regimens, thereby reducing patient long-term compliance issues.

In certain embodiments, the methods provided herein comprise performing immune system neuromodulation, thereby decreasing sympathetic immune system nerve activity. Immune system neuromodulation may be repeated one or more times at various intervals until a desired sympathetic nerve activity level or another therapeutic benchmark (e.g., target antibody titer, target white blood cell (WBC) count, etc.) is reached. In one embodiment, for example, a decrease in sympathetic nerve activity may be observed via a marker of sympathetic nerve activity such as plasma norepinephrine (noradrenaline) in autoimmune patients. Other measures or markers of sympathetic nerve activity can include muscle sympathetic nerve activity (MSNA), norepinephrine spillover, and/or heart rate variability.

In certain embodiments of the methods provided herein, immune system neuromodulation is expected to result in a decrease in sympathetic nerve activity over a specific timeframe. For example, in certain of these embodiments, sympathetic nerve activity levels are decreased over an extended timeframe, e.g., within about 1 month, 2 months, 3 months, 6 months, 9 months or 12 months post-neuromodulation.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline nerve activity level is derived from the subject undergoing treatment. For example, baseline nerve activity level may be measured in the subject at one or more timepoints prior to treatment. A baseline nerve activity value may represent sympathetic nerve activity at a specific timepoint before neuromodulation, or it may represent an average activity level at two or more timepoints prior to neuromodulation. In certain embodiments, the baseline value is based on nerve activity immediately prior to treatment (e.g., after the subject has already been catheterized). Alternatively, a baseline value may be derived from a standard value for nerve activity observed across the population as a whole or across a particular subpopulation. In certain embodiments, post-neuromodulation nerve activity levels are measured in extended timeframes post-neuromodulation, e.g., 3 months, 6 months or 12 months post-neuromodulation.

In certain embodiments of the methods provided herein, the methods are designed to decrease sympathetic nerve activity to a target level. In these embodiments, the methods include a step of measuring nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target nerve activity level is reached. In other embodiments, the methods are simply designed to decrease nerve activity below a baseline level without requiring a particular target activity level.

Immune system neuromodulation may be performed on a patient diagnosed with an immune system condition such as an autoimmune condition to reduce or prevent an increase in one or more measurable physiological parameters corresponding to the condition. In some embodiments, for example, immune system neuromodulation may prevent an increase in, maintain, or reduce the occurrence or severity of fatigue, fever, joint pain, stiffness, or swelling, skin lesions, blood markers of inflammation (e.g., ESR, hsCRP, IL-1, IL-6), new demyelinated lesions in the central nervous system (CNS), shortness of breath, chest pain, headaches, confusion, clumsiness, tingling, or weakness in patients diagnosed with an autoimmune condition. A reduction in a physiological parameter associated with an immune system condition may be determined by qualitative or quantitative analysis before and after (e.g., 1, 3, 6, or 12 months after) an immune system neuromodulation procedure.

As discussed previously, the progression of autoimmune conditions and other immune system conditions may be related to sympathetic overactivity and, correspondingly, the degree of sympathoexcitation in a patient may be related to the severity of the clinical presentation of the autoimmune condition and other immune system conditions. The nerves of the immune system may be positioned to be both a cause (via afferent nerve fibers) and a target (via efferent sympathetic nerves) of elevated central sympathetic drive. In some embodiments, immune system neuromodulation can be used to reduce central sympathetic drive in a patient diagnosed with an immune condition in a manner that treats the patient for the immune condition. In some embodiments, for example, MSNA can be reduced by at least about 10% in the patient within about three months after at least partially inhibiting sympathetic neural activity in nerves proximate an artery innervating an immune system organ. Similarly, in some instances immune system norepinephrine spillover to plasma can be reduced at least about 20% in the patient within about three months after at least partially inhibiting sympathetic neural activity in nerves proximate an artery innervating an immune system organ. Additionally, measured immune system norepinephrine content (e.g., assessed in real-time via intravascular blood collection techniques) can be reduced (e.g., by at least about 5%, 10%, or by at least 20%) in the patient within about three months after at least partially inhibiting sympathetic neural activity in nerves proximate an artery innervating an immune system organ.

In one prophetic example, a patient diagnosed with an autoimmune condition can be subjected to a baseline assessment indicating a first set of measurable parameters corresponding to the autoimmune condition. Such parameters can include, for example, antibody titers, WBC counts, blood markers of inflammation (e.g., ESR, hsCRP, IL-1, IL-6), imaging of the CNS for areas of demyelination, fatigue, fever, joint pain, stiffness, or swelling, skin lesions, shortness of breath, chest pain, headaches, confusion, clumsiness, tingling, or weakness. Following baseline assessment, the patient is subjected to an immune system neuromodulation procedure. Such a procedure can, for example, include any of the treatment modalities described herein or another treatment modality in accordance with the present technology. The treatment can be performed on nerves proximate the splenic artery, the splenic vein, and/or another portion of a vessel or duct of an immune system organ. Following the treatment (e.g., 1, 3, 6, or 12 months after treatment), the patient can be subjected to a follow-up assessment. The follow-up assessment can indicate a measurable improvement in one or more physiological parameters corresponding to the autoimmune condition. Additionally, one could measure the dose of immunosuppressant and immune modulating drugs required for maintenance therapy both before and after an immune system neuromodulation procedure, with a reduction in medications being deemed as a marker of successful therapy.

The methods described herein address the sympathetic excess that is thought to be an underlying cause of autoimmune conditions and other immune system conditions or a central mechanism through which these immune system conditions manifest their multiple deleterious effects on patients. In contrast, known therapies currently prescribed for autoimmune conditions and other immune system conditions typically address only specific manifestations of these conditions. Additionally, these known therapies can have significant limitations including limited efficacy, and frequently require the patient to remain compliant with the treatment regimen over time. In contrast, immune system neuromodulation can be a one-time treatment that would be expected to have durable benefits to inhibit the long-term disease progression and thereby achieve a favorable patient outcome. Unlike pharmacologic treatments that affect the entire body, it could also be a more targeted therapy, preferentially affecting the immune system organs.

In some embodiments, patients diagnosed with an immune system condition can be treated with immune system neuromodulation alone. However, in other embodiments patients diagnosed with autoimmune conditions and other immune system conditions can be treated with combinations of therapies for treating both primary causative modes of these conditions as well as sequelae of these conditions. For example, combinations of therapies can be tailored based on specific manifestations of the disease in a particular patient.

Treatment of an immune system condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

V. Selected Examples of Immune System Neuromodulation Systems and Devices

Figure 2:
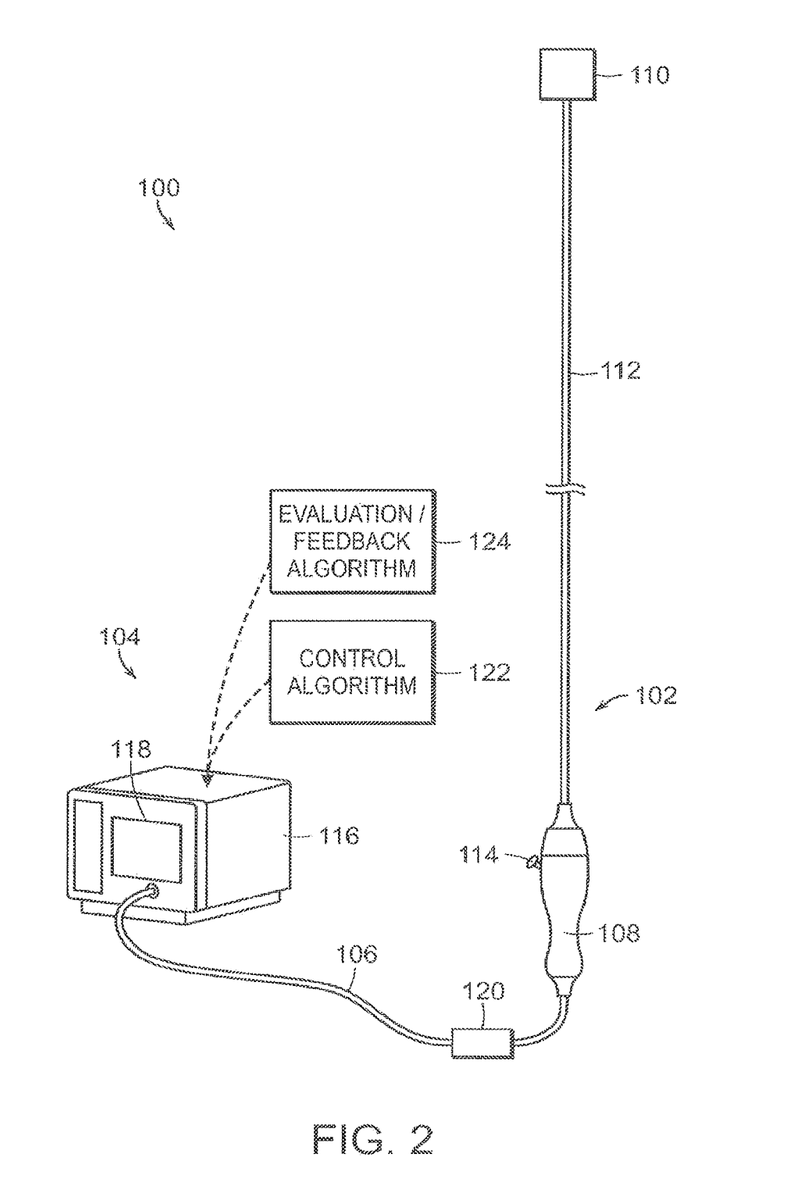
FIG. 2 is a partially schematic view illustrating a neuromodulation system configured in accordance with an embodiment of the present technology.

FIG. 2 is a partially schematic diagram illustrating an immune system neuromodulation system 100 ("system 100") configured in accordance with an embodiment of the present technology. The system 100 can include a treatment device 102, an energy source or console 104 (e.g., an RF energy generator, a cryotherapy console, etc.), and a cable 106 extending between the treatment device 102 and the console 104. The treatment device 102 can include a handle 108, a neuromodulation assembly 110, and an elongated shaft 112 extending between the handle 108 and the neuromodulation assembly 110. The shaft 112 can be configured to locate the neuromodulation assembly 110 intravascularly or intraluminally at a treatment location (e.g., in or near the splenic artery, the splenic vein, another portion of a vessel or duct of an immune system organ, and/or another suitable structure), and the neuromodulation assembly 110 can be configured to provide or support therapeutically-effective neuromodulation at the treatment location. In some embodiments, the shaft 112 and the neuromodulation assembly 110 can be 3, 4, 5, 6, or 7 French or another suitable size. Furthermore, the shaft 112 and the neuromodulation assembly 110 can be partially or fully radiopaque and/or can include radiopaque markers corresponding to measurements, e.g., every 5 cm.

Intravascular delivery can include percutaneously inserting a guide wire (not shown) within the vasculature and moving the shaft 112 and the neuromodulation assembly 110 along the guide wire until the neuromodulation assembly 110 reaches the treatment location. For example, the shaft 112 and the neuromodulation assembly 110 can include a guide-wire lumen (not shown) configured to receive the guide wire in an over-the-wire (OTW) or rapid-exchange configuration (RX). Other body lumens (e.g., ducts or internal chambers) can be treated, for example, by non-percutaneously passing the shaft 112 and neuromodulation assembly 110 through externally accessible passages of the body or other suitable methods. In some embodiments, a distal end of the neuromodulation assembly 110 can terminate in an atraumatic rounded tip or cap (not shown). The treatment device 102 can also be a steerable or non-steerable catheter device configured for use without a guide wire.

The neuromodulation assembly 110 can have a single state or configuration, or it can be convertible between a plurality of states or configurations. For example, the neuromodulation assembly 110 can be configured to be delivered to the treatment location in a delivery state and to provide or support therapeutically-effective neuromodulation in a deployed state. In these and other embodiments, the neuromodulation assembly 110 can have different sizes and/or shapes in the delivery and deployed states. For example, the neuromodulation assembly 110 can have a low-profile configuration in the delivery state and an expanded configuration in the deployed state. In another example, the neuromodulation assembly 110 can be configured to deflect into contact with a vessel wall in a delivery state. The neuromodulation assembly 110 can be converted (e.g., placed or transformed) between the delivery and deployed states via remote actuation, e.g., using an actuator 114 of the handle 108. The actuator 114 can include a knob, a pin, a lever, a button, a dial, or another suitable control component. In other embodiments, the neuromodulation assembly 110 can be transformed between the delivery and deployed states using other suitable mechanisms or techniques.

In some embodiments, the neuromodulation assembly 110 can include an elongated member (not shown) that can be configured to curve (e.g., arch) in the deployed state, e.g., in response to movement of the actuator 114. For example, the elongated member can be at least partially helical in the deployed state. In other embodiments, the neuromodulation assembly 110 can include a balloon (not shown) that can be configured to be at least partially inflated in the deployed state. An elongated member, for example, can be well suited for carrying one or more heating elements, electrodes, or transducers and for delivering direct heat, electrode-based, or transducer-based treatment. A balloon, for example, can be well suited for containing refrigerant (e.g., during or shortly after liquid-to-gas phase change) and for delivering cryotherapeutic treatment. In some embodiments, the neuromodulation assembly 110 can be configured for intravascular, transvascular, intraluminal, and/or transluminal delivery of chemicals. For example, the neuromodulation assembly 110 can include one or more openings (not shown), and chemicals (e.g., drugs or other agents) can be deliverable through the openings. For transvascular and transluminal delivery, the neuromodulation assembly 110 can include one or more needles (not shown) (e.g., retractable needles) and the openings can be at end portions of the needles.

The console 104 is configured to control, monitor, supply, or otherwise support operation of the treatment device 102. In other embodiments, the treatment device 102 can be self-contained and/or otherwise configured for operation without connection to the console 104. As shown in FIG. 1, the console 104 can include a primary housing 116 having a display 118. The system 100 can include a control device 120 along the cable 106 configured to initiate, terminate, and/or adjust operation of the treatment device 102 directly and/or via the console 104. In other embodiments, the system 100 can include another suitable control mechanism. For example, the control device 120 can be incorporated into the handle 108. The console 104 can be configured to execute an automated control algorithm 122 and/or to receive control instructions from an operator. Furthermore, the console 104 can be configured to provide feedback to an operator before, during, and/or after a treatment procedure via the display 118 and/or an evaluation/feedback algorithm 124. In some embodiments, the console 104 can include a processing device (not shown) having processing circuitry, e.g., a microprocessor. The processing device can be configured to execute stored instructions relating to the control algorithm 122 and/or the evaluation/feedback algorithm 124. Furthermore, the console 104 can be configured to communicate with the treatment device 102, e.g., via the cable 106. For example, the neuromodulation assembly 110 of the treatment device 102 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 108. The cable 106 can be configured to carry the signal from the handle 108 to the console 104.

The console 104 can have different configurations depending on the treatment modality of the treatment device 102. For example, when the treatment device 102 is configured for electrode-based or transducer-based treatment, the console 104 can include an energy generator (not shown) configured to generate RF energy, pulsed RF energy, microwave energy, optical energy, ultrasound energy (e.g., intravascularly delivered ultrasound, extracorporeal ultrasound, HIFU), magnetic energy, direct heat energy, or another suitable type of energy. In some embodiments, the console 104 can include an RF generator operably coupled to one or more electrodes (not shown) of the neuromodulation assembly 110. When the treatment device 102 is configured for cryotherapeutic treatment, the console 104 can include a refrigerant reservoir (not shown) and can be configured to supply the treatment device 102 with refrigerant, e.g., pressurized refrigerant in liquid or substantially liquid phase. Similarly, when the treatment device 102 is configured for chemical-based treatment, the console 104 can include a chemical reservoir (not shown) and can be configured to supply the treatment device 102 with one or more chemicals. In some embodiments, the treatment device 102 can include an adapter (not shown) (e.g., a luer lock) configured to be operably coupled to a syringe (not shown). The adapter can be fluidly connected to a lumen (not shown) of the treatment device 102, and the syringe can be used, for example, to manually deliver one or more chemicals to the treatment location, to withdraw material from the treatment location, to inflate a balloon (not shown) of the neuromodulation assembly 110, to deflate a balloon of the neuromodulation assembly 110, or for another suitable purpose. In other embodiments, the console 104 can have other suitable configurations.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

VI. Selected Examples of Treatment Procedures for Immune System Neuromodulation

Referring back to FIGS. 1B and 2B, in some embodiments the shaft 32 or 42 and the therapeutic element 34 or 44 can be portions of a treatment device at least partially corresponding to the treatment device 102 shown in FIG. 2. The therapeutic element 34 or 44, for example, can be configured to radially expand into a deployed state at the treatment location. In the deployed state, the therapeutic element 34 or 44 can be configured to contact an inner wall of a vessel and to form a suitable lesion or pattern of lesions without the need for repositioning. For example, the therapeutic element 34 or 44 can be configured to form a single lesion or a series of lesions, e.g., overlapping or non-overlapping. In some embodiments, the lesion or pattern of lesions can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the therapeutic element 34 or 44 can be configured cause a partially-circumferential lesion or a fully-circumferential lesion at a single longitudinal segment or zone of the vessel. During treatment, the therapeutic element 34 or 44 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the therapeutic element 34 or 44 can be configured to form therapeutically-effective neuromodulation (e.g., using ultrasound energy) without contacting a vessel wall.

A variety of other suitable treatment locations are also possible in and around the splenic artery 38 and 48, splenic branch arteries 30 and 40, splenic vein, other portions of vessels or ducts of immune system organs, and/or other suitable structures. For example, in some cases, it can be more convenient to treat the splenic artery 38 or 48 at its trunk, where it meets the celiac artery. It may also be possible to achieve the desired denervation by targeting the celiac artery, but in such a case one would need to demonstrate that modulating the nerves did not cause significant adverse consequences in other structures receiving innervation from nerves proximate to the celiac trunk.

Furthermore, a treatment procedure can include treatment at any suitable number of treatment locations, e.g., a single treatment location, two treatment locations, or more than two treatment locations. In some embodiments, different treatment locations can correspond to different portions of the splenic artery 38 or 48, the splenic branch arteries 30 or 40, the splenic vein, other portions of vessels and ducts of immune system organs, and/or other suitable structures proximate tissue having relatively high concentrations of immune system nerves. The shaft 32 or 42 can be steerable (e.g., via one or more pull wires, a steerable guide or sheath catheter, etc.) and can be configured to move the therapeutic element 34 or 44 between treatment locations. At each treatment location, the therapeutic element 34 or 44 can be activated to cause modulation of nerves proximate the treatment location. Activating the therapeutic element 34 or 44 can include, for example, heating, cooling, stimulating, or applying another suitable treatment modality at the treatment location. Activating the therapeutic element 34 or 44 can further include applying various energy modalities at varying power levels or intensities or for various durations for achieving modulation of nerves proximate the treatment location. In some embodiments, power levels, intensities, and/or treatment duration can be determined and employed using various algorithms for ensuring modulation of nerves at select distances (e.g., depths) away from the treatment location. Furthermore, as noted previously, in some embodiments, the therapeutic element 34 or 44 can be configured to introduce (e.g., inject) a chemical (e.g., a drug or another agent) into target tissue at the treatment location. Such chemicals or agents can be applied at various concentrations depending on treatment location and the relative depth of the target nerves.

The splenic artery branches off the celiac artery, which in turn branches from the abdominal aorta, so the least invasive access route for the therapeutic element 34 or 44 to be positioned at a treatment location within the splenic artery would typically be through femoral, brachia!, or radial access to the abdominal aorta. However, other suitable catheterization paths may be used. Catheterization can be guided, for example, using imaging, e.g., magnetic resonance, computed tomography, fluoroscopy, ultrasound, intravascular ultrasound, optical coherence tomography, or another suitable imaging modality. The therapeutic element 34 or 44 can be configured to accommodate the anatomy of the splenic artery 38 or 48, splenic branch artery 30 or 40, the splenic vein, another portion of a vessel or duct of an immune system organ, and/or another suitable structure. For example, the therapeutic element 34 or 44 can include a balloon (not shown) configured to inflate to a size generally corresponding to the internal size of the splenic artery 38 or 48, splenic branch artery 30 or 40, splenic vein, another portion of a vessel or duct of an immune system organ, and/or another suitable structure. In some embodiments, the therapeutic element 34 or 44 can be an implantable device and a treatment procedure can include locating the therapeutic element 34 or 44 at the treatment location using the shaft 32 or 42, fixing the therapeutic element 34 or 44 at the treatment location, separating the therapeutic element 34 or 44 from the shaft 32 or 42, and withdrawing the shaft 32 or 42. Other treatment procedures for modulation of immune system nerves in accordance with embodiments of the present technology are also possible.

As mentioned previously, the methods disclosed herein may use a variety of suitable energy modalities, including RF energy, pulsed RF energy, microwave energy, laser energy, optical energy, ultrasound energy (e.g., intravascularly delivered ultrasound, extracorporeal ultrasound, HIFU), magnetic energy, direct heat, cryotherapy, or a combination thereof. Alternatively or in addition to these techniques, the methods may utilize one or more non-ablative neuromodulatory techniques. For example, the methods may utilize non-ablative SNS denervation by removal of target nerves, injection of target nerves with a destructive drug or pharmaceutical compound, or treatment of the target nerves with non-ablative energy modalities. In certain embodiments, the amount of reduction of the sympathetic nerve activity may vary depending on the specific technique being used.

In one example, the treatment device 102 set forth in FIG. 2 can be an RF energy emitting device and RF energy can be delivered through energy delivery elements or electrodes to one or more locations along the inner wall of a first immune system blood vessel (e.g., a splenic artery or vein) for predetermined periods of time (e.g., 120 seconds). An objective of a treatment may be, for example, to heat tissue to a desired depth (e.g., at least about 3 mm) to a temperature (e.g., about 65° C.) that would modulate one or more nerve fibers associated with or adjacent to one or more lesions formed in the vessel wall. A clinical objective of the procedure typically is to neuromodulate a sufficient number of immune system nerves (efferent and/or afferent nerves) to cause a reduction in sympathetic tone or drive to one or more immune system organs without, for example, disrupting immune system function and while minimizing vessel trauma. If the objective of a treatment is met (e.g., tissue is heated to about 65° C. to a depth of about 3 mm) the probability of modulating immune system nerve tissue (e.g., altering nerve function) is high. In some embodiments, a single neuromodulation treatment procedure can provide for sufficient modulation of target sympathetic nerves (e.g., modulation of a sufficient number of nerve fibers) to provide a desired clinical outcome. In other embodiments, more than one treatment may be beneficial for modulating a desired number or volume of target nerve fibers, and thereby achieving clinical success. In other embodiments, an objective may include reducing or eliminating immune system nerve function completely.

In a specific example of using RF energy for immune system nerve modulation, a clinician can commence treatment, which causes the control algorithm 122 (FIG. 2) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time, i.e., in a linear manner. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts, or in a further embodiment, $P_{MAX}$ is 6.5 watts. In some embodiments, $P_{MAX}$ can be about 6 watts to about 10 watts. Optionally, the power may be maintained at the maximum power $P_{MAX}$ for a desired period of time or up to the desired total treatment time (e.g., up to about 120 seconds), or until a specified temperature is reached or maintained for a specified time period.

In another specific example, the treatment device 102 in FIG. 2 can be a cryogenic device and cryogenic cooling can be applied for one or more cycles (e.g., for 30 second increments, 60 second increments, 90 second increments, etc.) in one or more locations along the circumference and/or length of the first immune system blood vessel. The cooling cycles can be, for example, fixed periods or can be fully or partially dependent on detected temperatures (e.g., temperatures detected by a thermocouple (not shown) of the neuromodulation assembly 110). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 110 can then be located at a second target site in or near a second immune system blood vessel (e.g., a splenic artery or vein), and correct positioning of the assembly 110 can be determined. In selected embodiments, a contrast material can be delivered distally beyond the neuromodulation assembly 110 and fluoroscopy and/or other suitable imaging techniques can be used to locate the second immune system vessel. The method continues by applying targeted heat or cold to effectuate immune system neuromodulation at the second target site to cause partial or full denervation of the immune system organ associated with the second target site.

After providing the therapeutically-effective neuromodulation energy (e.g., cryogenic cooling, RF energy, ultrasound energy, etc.), the method may also include determining whether the neuromodulation therapeutically treated an immune system condition, a condition associated with sympathetic activity in an immune system organ, or a condition associated with central sympathetic activity or otherwise sufficiently modulated nerves or other neural structures proximate the first and second target sites. For example, the process of determining whether the neuromodulation therapeutically treated the nerves can include determining whether nerves were sufficiently modulated or otherwise disrupted to reduce, suppress, inhibit, block or otherwise affect the afferent and/or efferent immune system signals (e.g., by evaluation of suitable biomarkers, stimulation and recording of nerve signals, etc.). In a further embodiment, patient assessment could be performed at time intervals (e.g., 1 month, 3 months, 6 months, 12 months) following neuromodulation treatment. For example, the patient can be assessed for measurements of perceived fatigue, fever, joint pain, stiffness, or swelling, skin lesions, shortness of breath, chest pain, headaches, confusion, clumsiness, tingling, or weakness, or for one or more physiological parameters selected from, for example, MSNA, norepinephrine spillover to plasma, whole body norepinephrine spillover, heart rate variability, antibody titer, or WBC count.

In other embodiments, various steps in the method can be modified, omitted, and/or additional steps may be added. In further embodiments, the method can have a delay between applying therapeutically-effective neuromodulation energy at a first target site at or near a first immune system blood vessel and applying therapeutically-effective neuromodulation energy at a second target site at or near a second immune system blood vessel. For example, neuromodulation of the first immune system blood vessel can take place at a first treatment session, and neuromodulation of the second immune system blood vessel can take place at a second treatment session at a later time.

As discussed previously, treatment procedures for modulation of immune system nerves in accordance with embodiments of the present technology are expected to improve at least one condition associated with an immune system condition and/or with sympathetic activity in an immune system organ or a condition associated with central sympathetic activity. For example, with respect to an autoimmune condition, modulation of immune system nerves in accordance with embodiments of the present technology is expected to reduce, maintain, or prevent an increase in fatigue, fever, joint pain, stiffness, or swelling, skin lesions, shortness of breath, chest pain, headaches, confusion, clumsiness, tingling, or weakness. With respect to central sympathetic activity (e.g., overactivity or hyperactivity), for example, modulation of immune system nerves is expected to reduce MSNA and/or whole body norepinephrine spillover in patients. These and other clinical effects are expected to be detectable immediately after a treatment procedure or after a delay, e.g., of 1, 2, or 3 months. In some embodiments, it may be useful to repeat immune system neuromodulation at the same treatment location or a different treatment location after a suitable delay, e.g., 1, 2, or 3 years. In still other embodiments, however, other suitable treatment regimens or techniques may be used.

VII. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with immune system neuromodulation.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the CNS. Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho•adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 3:
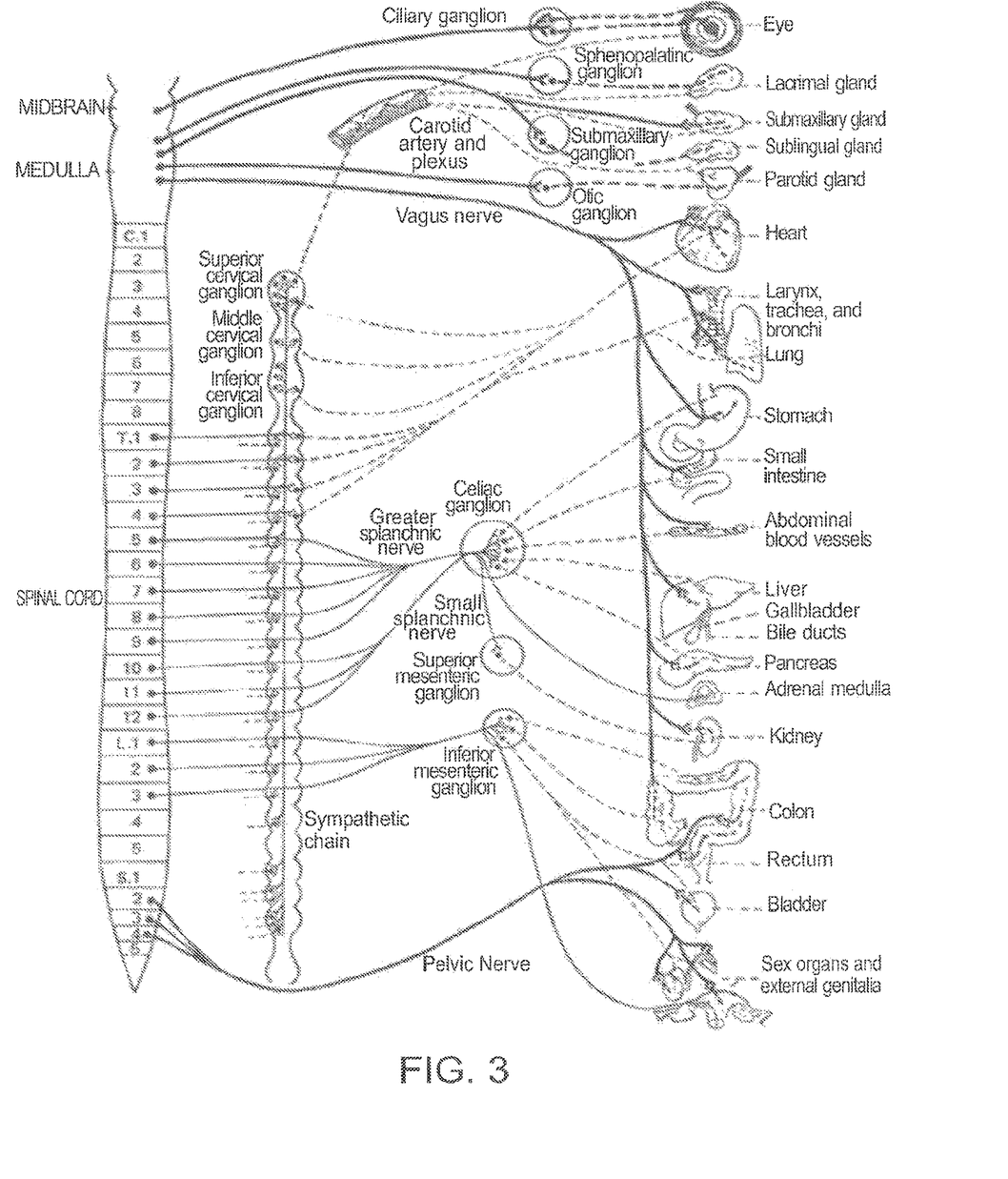
FIG. 3 is a conceptual illustration of the SNS and how the brain communicates with the body via the SNS.

As shown in FIG. 3, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

Further Examples

1. A method of treating a human patient diagnosed with an immune system condition, the method comprising:
   intravascularly positioning a neuromodulation assembly within an immune system blood vessel of the patient and adjacent to a target immune system nerve of the patient; and
   reducing sympathetic neural activity in the patient by delivering energy to the immune system nerve via the neuromodulation assembly to modulate a function of the immune system nerve,
   wherein reducing sympathetic neural activity improves a measurable physiological parameter corresponding to the immune system condition of the patient.

2. The method of example 1 wherein the immune system condition is an autoimmune condition.

3. The method of example 2 wherein the autoimmune condition is selected from the group consisting of multiple sclerosis, lupus, and psoriasis.

4. The method of any one of examples 1-3 wherein reducing sympathetic neural activity in the patient in a manner that improves a measurable physiological parameter corresponding to the immune system condition comprises reducing muscle sympathetic nerve activity in the patient.

5. The method of any one of examples 1-3 wherein reducing sympathetic neural activity in the patient in a manner that improves a measurable physiological parameter corresponding to the immune system condition comprises reducing whole body norepinephrine spillover in the patient.

6. The method of any one of examples 1-5 wherein intravascularly positioning a neuromodulation assembly within an immune system blood vessel comprises positioning the neuromodulation assembly in at least one of the splenic artery, splenic branch artery, or splenic vein.

7. The method of any one of examples 1-6 wherein reducing sympathetic neural activity in the patient by delivering energy to the immune system nerve comprises at least partially inhibiting afferent neural activity.

8. The method of any one of examples 1-6 wherein reducing sympathetic neural activity in the patient by delivering energy to the immune system nerve comprises at least partially inhibiting efferent neural activity.

9. The method of any one of examples 1-8 wherein reducing sympathetic neural activity in the patient by delivering energy to the immune system nerve comprises partially ablating the target immune system nerve.

10. The method of any one of examples 1-9 wherein reducing sympathetic neural activity in the patient by delivering energy to the immune system nerve via the neuromodulation assembly comprises delivering an energy field to the target immune system nerve via the neuromodulation assembly.

11. The method of example 10 wherein delivering an energy field to the target immune system nerve comprises delivering radio frequency (RF) energy via the neuromodulation assembly.

12. The method of example 10 wherein delivering an energy field to the target immune system nerve comprises delivering ultrasound energy via the neuromodulation assembly.

13. The method of example 12 wherein delivering ultrasound energy comprises delivering high intensity focused ultrasound energy via the neuromodulation assembly.

14. The method of example 10 wherein delivering an energy field to the target immune system nerve comprises delivering laser energy via the neuromodulation assembly.

15. The method of example 10 wherein delivering an energy field to the target immune system nerve comprises delivering microwave energy via the neuromodulation assembly.

16. The method of any one of examples 1-15, further comprising removing the neuromodulation assembly from the patient after delivering energy to the immune system nerve via the neuromodulation assembly to modulate a function of the immune system nerve.

17. A method, comprising:
percutaneously introducing a neuromodulation assembly at a distal portion of a treatment device proximate to neural fibers innervating an immune system organ of a human subject diagnosed with an immune system condition;
partially disrupting function of the neural fibers via the neuromodulation assembly; and removing the neuromodulation assembly from the subject after treatment, wherein partial disruption of the function of the neural fibers therapeutically treats one or more symptoms associated with the immune system condition of the subject.

18. The method of example 17 wherein partially disrupting function of the neural fibers via the neuromodulation assembly comprises delivering a chemical agent to tissue at a treatment location proximate the neural fibers in a manner that modulates sympathetic neural activity of the neural fibers.

19. The method of example 17 wherein partially disrupting function of the neural fibers via the neuromodulation assembly comprises thermally modulating the neural fibers via at least one wall-contact electrode.

20. The method of example 17 wherein partially disrupting function of the neural fibers via the neuromodulation assembly comprises thermally modulating the neural fibers via a multi-electrode array positioned within an immune system blood vessel of the patient.

22. The method of example 17 wherein partially disrupting function of the neural fibers via the neuromodulation assembly comprises cryotherapeutically cooling the neural fibers via the neuromodulation assembly.

22. A device for carrying out the method of any of examples 1-21.

CONCLUSION

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while steps may be presented in a given order, alternative embodiments may perform steps in a different order. The various embodiments described herein and elements thereof may also be combined to provide further embodiments. In some cases, well-known structures and functions have not been shown or described in detail to avoid unnecessarily obscuring the description of embodiments of the present technology.

Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout the disclosure to mean including at least the recited feature(s) such that any greater number of the same feature(s) and/or additional types of other features are not precluded. It will also be appreciated that various modifications may be made to the described embodiments without deviating from the present technology. Further, while advantages associated with certain embodiments of the present technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

What is claimed is:

1. A method of treating an autoimmune condition associated with inflammation, the method comprising:
intravascularly positioning a neuromodulation catheter having an energy delivery element at a treatment location within a splenic artery, a splenic branch artery, a splenic vein, or a splenic branch vein of the patient;

delivering neuromodulation energy to neural fibers proximate the splenic artery, the splenic branch artery, the splenic vein, or the splenic branch vein of the patient to reduce inflammation and modulate an immune response; and repeating neuromodulation at the treatment location until a level or activity of one or more markers of inflammation including interleukins, high-sensitivity C-reactive proteins, erythrocyte sedimentation rate (ESR) or heat shock proteins reaches a benchmark.

2. The method of claim 1, wherein the autoimmune condition includes multiple sclerosis, lupus or psoriasis.

3. The method of claim 1, wherein delivering the neuromodulation energy reduces or prevents an increase in the level or activity of the one or more markers of inflammation.

4. The method of claim 1, further comprising:
measuring the level or activity of the one or more markers of inflammation after delivery of the neuromodulation energy; and
comparing the level or activity to a baseline activity level that is measured prior to delivery of the neuromodulation energy.

5. The method of claim 4, wherein the baseline activity level represents an average activity level at two or more timepoints prior to delivery of the neuromodulation energy.

6. The method of claim 4, further comprising:
measuring the level or activity of the one or more markers of inflammation prior to delivery of the neuromodulation energy.

7. The method of claim 1, wherein delivering the neuromodulation energy results in a reduction in occurrence of a severity of fatigue, fever, joint pain, stiffness, swelling, skin lesions, new demyelinated lesions, shortness of breath, chest pain, headaches, confusion, clumsiness, tingling or weakness.

8. A method of treating an autoimmune condition associated with inflammation, the method comprising:
intravascularly positioning a neuromodulation catheter having an energy delivery element at a treatment location within a splenic artery, a splenic branch artery, a splenic vein, or a splenic branch vein of the patient;
delivering neuromodulation energy to neural fibers proximate the splenic artery, the splenic branch artery, the splenic vein, or the splenic branch vein of the patient to reduce inflammation and modulate an immune response, wherein the delivery of the neuromodulation energy improves a level or activity of one or more markers of inflammation; and
repeating neuromodulation at the treatment location until the level or activity of one or more markers of inflammation reaches a benchmark.

9. The method of claim 8, wherein the autoimmune condition includes multiple sclerosis, lupus or psoriasis.

10. The method of claim 8, wherein delivering the neuromodulation energy reduces or prevents an increase in the level or activity of the one or more markers of inflammation.

11. The method of claim 8, further comprising:
measuring the level or activity of the one or more markers of inflammation after delivery of the neuromodulation energy; and
comparing the level or activity to a baseline activity level that is measured prior to delivery of the neuromodulation energy.

12. The method of claim 8, wherein the baseline activity level represents an average activity level at two or more timepoints prior to delivery of the neuromodulation energy.

13. The method of claim 8, further comprising:
measuring the level or activity of the one or more markers of inflammation prior to delivery of the neuromodulation energy.

14. The method of claim 8, wherein delivering the neuromodulation energy results in a reduction in occurrence of a severity of fatigue, fever, joint pain, stiffness, swelling, skin lesions, new demyelinated lesions, shortness of breath, chest pain, headaches, confusion, clumsiness, tingling or weakness.

15. The method of claim 8, wherein delivering neuromodulation energy to the neural fibers includes delivering radio frequency (RF) energy via the energy delivery element.

16. A method of treating an autoimmune condition associated with inflammation, the method comprising:
intravascularly positioning a neuromodulation catheter having an energy delivery element at a treatment location within a splenic artery, a splenic branch artery, a splenic vein, or a splenic branch vein of the patient;
delivering radio frequency energy to neural fibers proximate the splenic artery, the splenic branch artery, the splenic vein, or the splenic branch vein of the patient to reduce inflammation and modulate an immune response; and
repeating neuromodulation at the treatment location until a level or activity of one or more markers of inflammation including interleukins, high-sensitivity C-reactive proteins, erythrocyte sedimentation rate (ESR) or heat shock proteins reaches a benchmark.

17. The method of claim 16, wherein the autoimmune condition includes multiple sclerosis, lupus or psoriasis.

18. The method of claim 16, wherein delivering the neuromodulation energy reduces or prevents an increase in the level or activity of the one or more markers of inflammation.

19. The method of claim 16, further comprising:
measuring the level or activity of the one or more markers of inflammation after delivery of the neuromodulation energy; and
comparing the level or activity to a baseline activity level that is measured prior to delivery of the neuromodulation energy.

20. The method of claim 16, further comprising:
measuring the level or activity of the one or more markers of inflammation prior to delivery of the neuromodulation energy.

* * * * *